(12) United States Patent
Viswanathan et al.

(10) Patent No.: US 7,742,803 B2
(45) Date of Patent: *Jun. 22, 2010

(54) VOICE CONTROLLED USER INTERFACE FOR REMOTE NAVIGATION SYSTEMS

(75) Inventors: Raju R. Viswanathan, St. Louis, MO (US); Jeffrey M. Garibaldi, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1083 days.

This patent is subject to a terminal disclaimer.

(21) Appl. No.: 11/429,667

(22) Filed: May 5, 2006

(65) Prior Publication Data

US 2006/0281989 A1  Dec. 14, 2006

Related U.S. Application Data

(60) Provisional application No. 60/678,320, filed on May 6, 2005.

(51) Int. Cl.
*A61B 5/05* (2006.01)

(52) U.S. Cl. ............... 600/424; 600/407; 600/427; 128/899

(58) Field of Classification Search ............ 600/407, 600/410, 423, 424, 426, 130, 117, 373, 427, 600/508; 378/20, 205; 324/309, 207.13, 324/207.22, 260; 128/897, 898, 899
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |

(Continued)

*Primary Examiner*—Brian Casler
*Assistant Examiner*—Elmer Chao
(74) *Attorney, Agent, or Firm*—Harness, Dickey & Pierce, P.L.C.

(57) ABSTRACT

A method of controlling a remote navigation system that remotely orients the distal end of the medical device in order to navigate a medical device through a body lumen, the method comprising: displaying an exterior image of the body lumen; superimposing an indicator of the current position of the medical device in the body lumen; displaying a plurality of segment labels; receiving oral commands and recognizing one of the spoken displayed segment labels; and causing the remote navigation system to orient the distal end of the device in a preselected direction associated with the segment corresponding to the displayed segment label.

27 Claims, 4 Drawing Sheets

U.S. PATENT DOCUMENTS

| | | |
|---|---|---|
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,785,593 B2 | 8/2004 | Wang et al. .................. 700/758 |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,127,401 B2 | 10/2006 | Miller .................. 704/275 |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2003/0125752 A1* | 7/2003 | Werp et al. .................. 606/108 |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |

* cited by examiner

VOICE CONTROLLED USER INTERFACE FOR REMOTE NAVIGATION SYSTEMS

CROSS-REFERENCE TO RELATED APPLICATIONS

This application claims the benefit of U.S. Provisional Patent Application Ser. No. 60/678,320, filed May 6, 2005, the entire disclosure of which is incorporated herein by reference.

BACKGROUND OF THE INVENTION

This invention relates to the remote navigation of medical devices in the body, and in particular to the control of remote navigation systems.

Remote navigation systems have been developed that allow a user to remotely control the orientation of the distal end of a medical device to facilitate navigation of the device through the body. Examples of such systems include the magnetic navigation systems made by Stereotaxis, Inc., St. Louis, Mo., which create a magnetic field in a selected direction to orient the distal end of a medical device having one or more magnetically responsive elements. Other examples of remote navigation systems include robotic systems, such as systems using motors or mechanical devices such as pull wires or push wires to move articulated members. The technology of remote navigation systems has advanced to a point where they can quickly and easily orient the distal end of a medical device in a selected direction, but regardless of the method of movement an obstacle to their wide spread use is difficulties indicating to the remote navigation system the desired direction in which to orient the medical device.

A variety of interfaces have been created to facilitate the communication of the desired direction of orientation from the user to the remote navigation system. For example the magnetic navigation systems available from Stereotaxis, Inc. have a number of tools to help the user select the direction for the medical device and cause the magnetic navigation system to align in the selected direction. These interfaces typically require the user to manipulate a cursor on a display or actuate a touch screen. This can be difficult where the user is also trying to manually advance the medical device, or is otherwise using his or her hands.

SUMMARY OF THE INVENTION

Embodiments of the methods and interfaces in accordance with the principles of the present invention provide a method of controlling a remote navigation system to orient a medical device in a selected direction. A preferred embodiment of the methods of this invention comprises displaying an exterior image of the body lumen; superimposing an indicator of the current position of the medical device in the body lumen; displaying a plurality of segment labels each corresponding to a segment of the image and having a predetermined direction associated therewith; receiving oral commands and recognizing one of the oral commands as one of the displayed segment labels; causing the remote navigation system to orient the distal end of the device in the preselected direction associated with the segment corresponding to the displayed segment label.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figure 1:
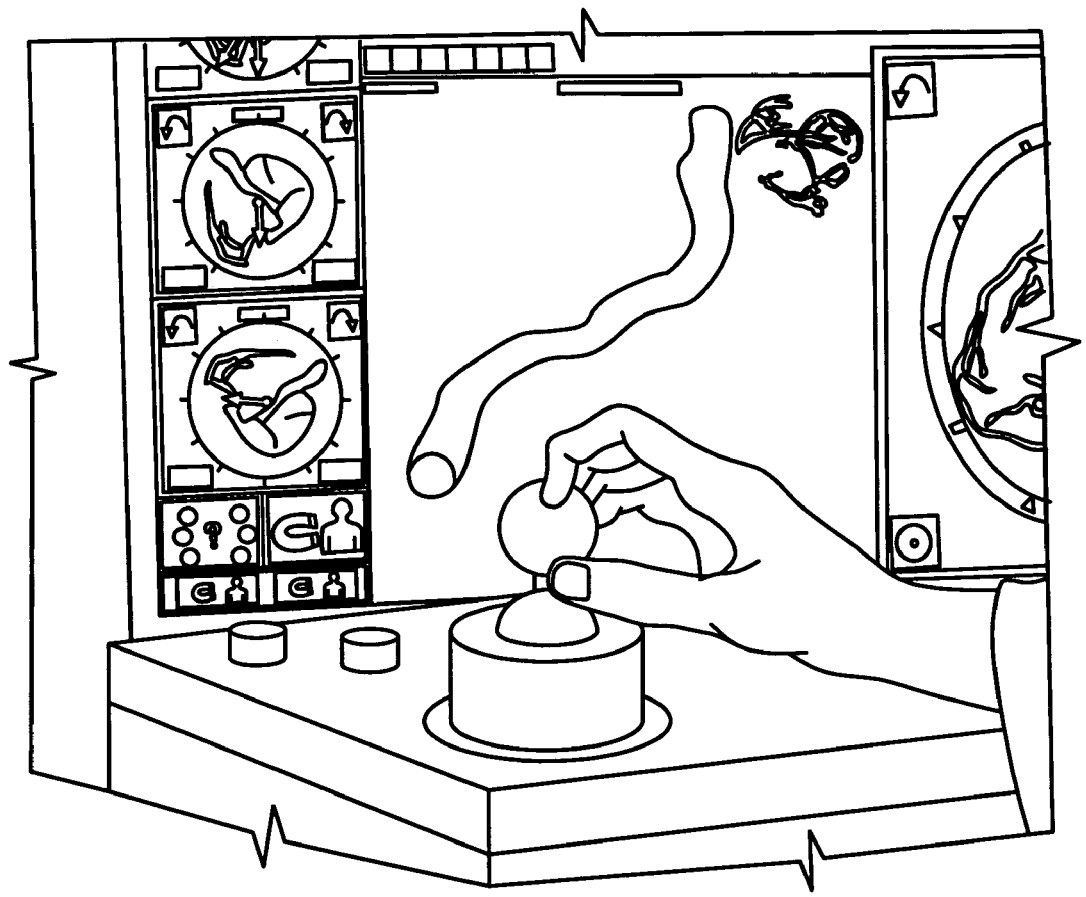
FIG. 1 is a view of a manually operated interface for controlling the orientation of the distal end of a medical device with a joy stick.
Figure 2:
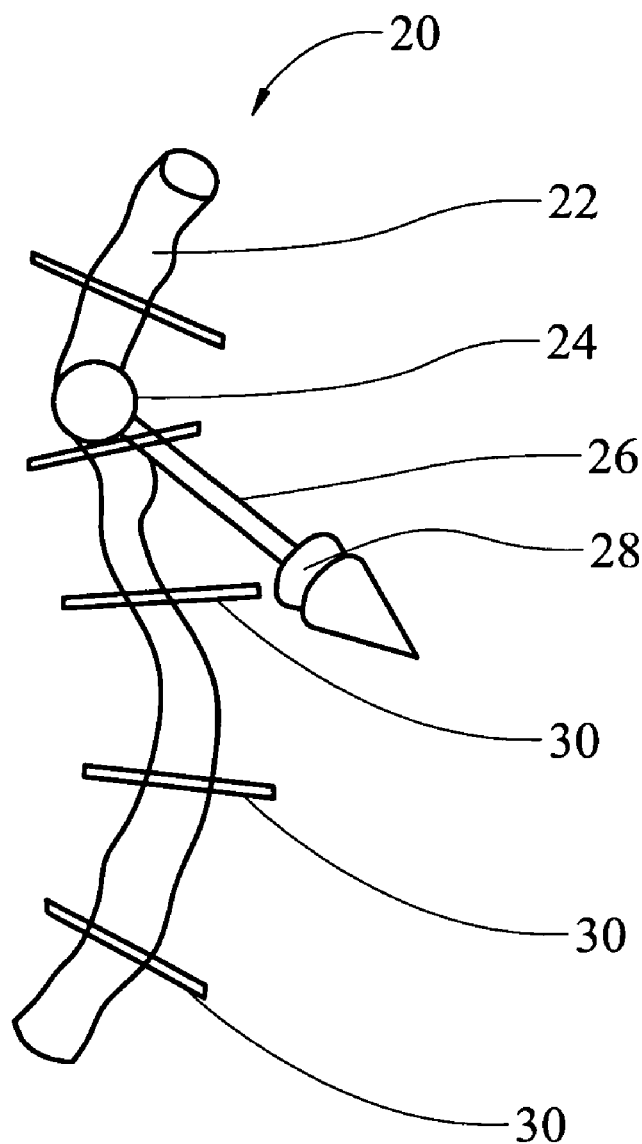
FIG. 2 is a view of section of an exemplary body lumen or cavity through which a remote navigation system will be used to navigate a medical device.

A preferred embodiment of an interface implementing methods in accordance with the principles of this invention is illustrated in FIG. 2. As shown in FIG. 2, the interface includes a display 20 on which an image 22 of the body lumen or cavity through which the device is being navigated is displayed. The image 22 may be an actual image obtained from x-ray or fluoroscopic imaging, CT imaging, MR imaging, ultrasonic imaging or any other imaging modality. The image 22 may also be a constructed imaging reconstructed from imaging data obtained from x-ray or fluoroscopic imaging, CT imaging, MR imaging, ultrasonic imaging or any other imaging modality. Also shown in FIG. 2 is a marker 24 indicating the current position of the distal end of the medical device being navigated through the body lumen or cavity. A yellow arrow 26 and a green arrow 28 are also shown, and are a feature of the magnetic navigation system with which the interface is being used. The green arrow 28 indicates the current direction of the magnetic field being applied by magnetic navigation system and the yellow arrow 26 indicated the direction of the magnetic field to be applied by the magnetic navigation system. While described and illustrated in conjunction with a magnetic navigation system, the interface and methods of the present invention are not so limited, and apply to other remote navigation systems, including but not limited to mechanical or electrical navigation systems, or combinations of any of these.

In accordance with the principles of this invention, the image data is processed, and the image is divided into a plurality of segments of similar direction. For example, as shown in FIG. 2 the system may automatically divide the image into segments in which the direction (e.g. the centerline direction) does not vary by more than a predetermined amount, e.g., 3° or 5°. These segments may be identified with dividers 30, or they can be identified by other visual indicators, including symbols or color coding. The system preferably automatically suggests unique labels to identify the segments. The automatic labeling helps to prevent injudicious choices of segment names by users which the system may have difficulty recognizing.

The system may alternatively allow the user to name the sections. In this case, the system might prompt the user to type in a name for each section and use text to voice technology to recognize the assigned names when subsequently spoken. The system might alternatively prompt the user to speak the name of each section and either use voice recognition software to store the names, or store the audio information for subsequent comparison.

The system assigns each of the sections at least one direction. This direction may be an average centerline direction for the section, or it may be the direction of the centerline at the midpoint, or it may be the direction of the center line at the proximal or the distal end. The system could also be some sort of composite direction.

The system is adapted to receive and process oral commands, and in accordance with the principles of this invention, is adapted to receive an oral identification from the user of a particular section. Upon confirmation of the identified section, the system then operates the remote navigation system to orient the distal end of the device in the direction corresponding to the identified section. The current location of the medical device is preferably identified on the display, such as with marker 24, and as the distal end of the device moves from section to section, the user can properly orient the device for its current or for its next section simply by orally stating the name of the section that the device is in or to which the device is being moved. The system automatically causes the remote navigation system to change the orientation of the device to an orientation appropriate to the section specified by the user.

Validation of orally issued commands usually is important in a voice controlled system. The system preferably tracks the position of the medical device, and therefore can be programmed to anticipate that the next direction command will correspond to the next section in the distal direction, or in the case of a branched lumen, to one of a limited number of next sections in the distal direction. Thus the system can more accurately discriminate voice commands than if the voice command could be any one of a larger number of commands. However, if validation is desired or required, a validation scheme can be provided to confirm the voice commands. For example, upon receipt of a voice command identifying a particular direction, the system can highlight the selection it corresponds to the voice command is received and before proceeding wait for a validation command, such as "YES" or "CORRECT". Alternatively, if the user is observing the device on an X-ray image, pressing the Fluoro pedal could be taken to be a confirmation of the voice command. In this case, either the action of pressing the Fluoro pedal, or the fact of the Fluoro pedal being pressed for a certain pre-determined time interval, could be used as command confirmation.

Figure 4:
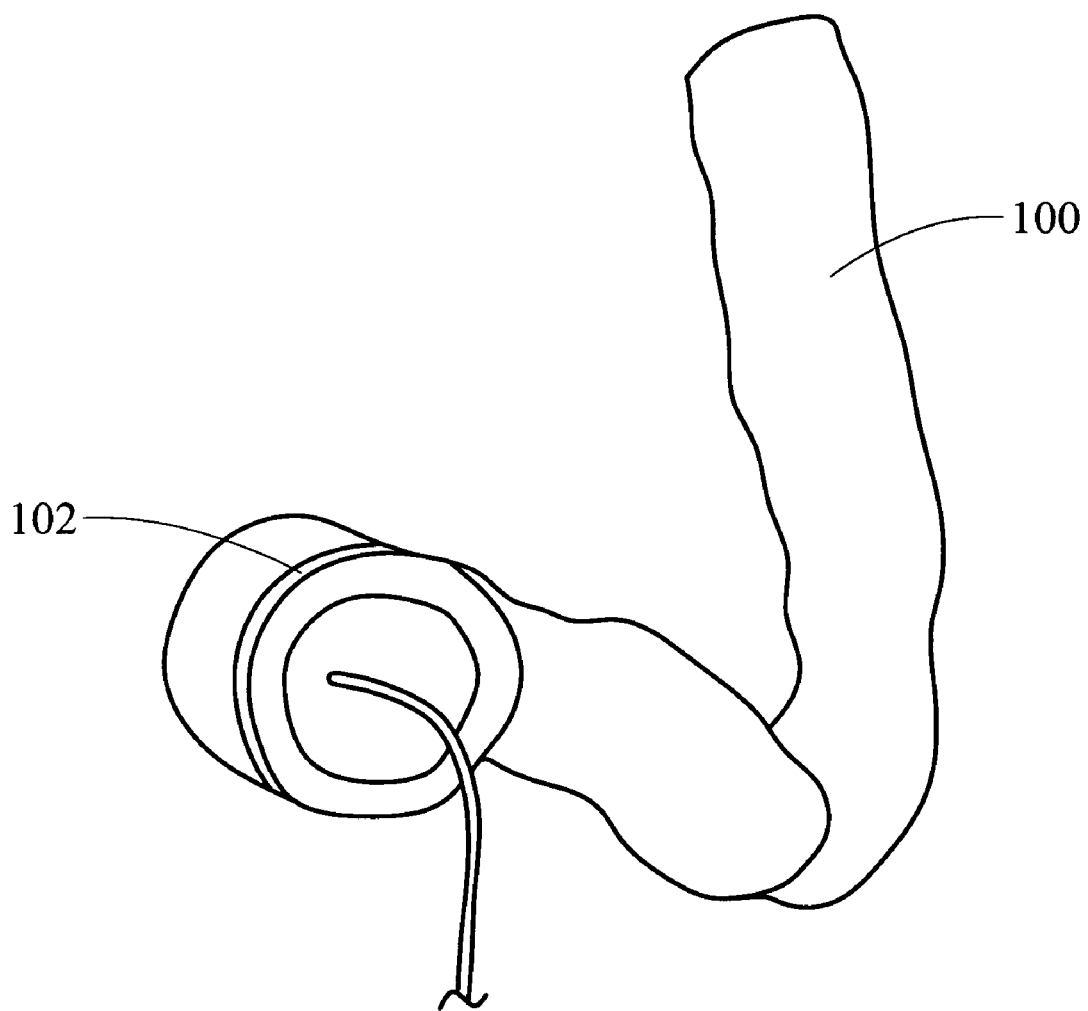
FIG. 4 is a view of the section of the exemplary body lumen, showing the navigation of a medical device with a remote navigation system.

It is extremely helpful to navigation in accordance with the principles of this invention that the user accurately understand the current position of the medical device. When navigating through a reconstructed body lumen or cavity it might not be immediately apparent. Thus, as shown in FIG. 4, the current position of the medical device can be displayed as a ring on the surface of the lumen or cavity. The ring is preferably in plane perpendicular to the centerline of the lumen or cavity at the location of the distal tip of the device.

To facilitate the navigation of a medical device through body lumens and cavities, it is desirable to clearly indicate to the physician or other user where the distal end of the device is presently located. Thus in accordance with one embodiment of the present invention, an external image 100 of a body lumen or cavity is displayed. The position of the medical device is determined by any conventional means of localization, including using signals, electrostatic localization, optical localization, image processing localization, etc. In the case of navigating through a relatively constricted lumen, such as a blood vessel, the position in the vessel can be determined by measuring the extended length of the device, as advancement of a given length will substantially correspond to the same advancement along the centerline of the vessel. The advancement of the medical device can be measured in a number of ways. If the device is advanced by machine, for example opposed rollers as disclosed in U.S. patent application Ser. No. 10/138,710, filed May 3, 2002, and U.S. patent application Ser. No. 10/858,485, filed Jun. 1, 2004, (the disclosures of which are incorporated by reference), then the rotation of the rollers can be used to measure the advancement of device. Alternatively, marks can be provided on the device which can be physically, electrically, optically, or otherwise sensed to measure the advancement of the medical device.

As shown in FIG. 4, a ring 102 is superimposed on the displayed image of the body lumen corresponding to the position of the distal end of the medical device. This ring is positioned in the plane perpendicular to the centerline of the lumen at the location of distal end of the medical device. The ring 102 on the image 100 helps the physician visualize the current location of the medical device.

Operation

Figure 3:
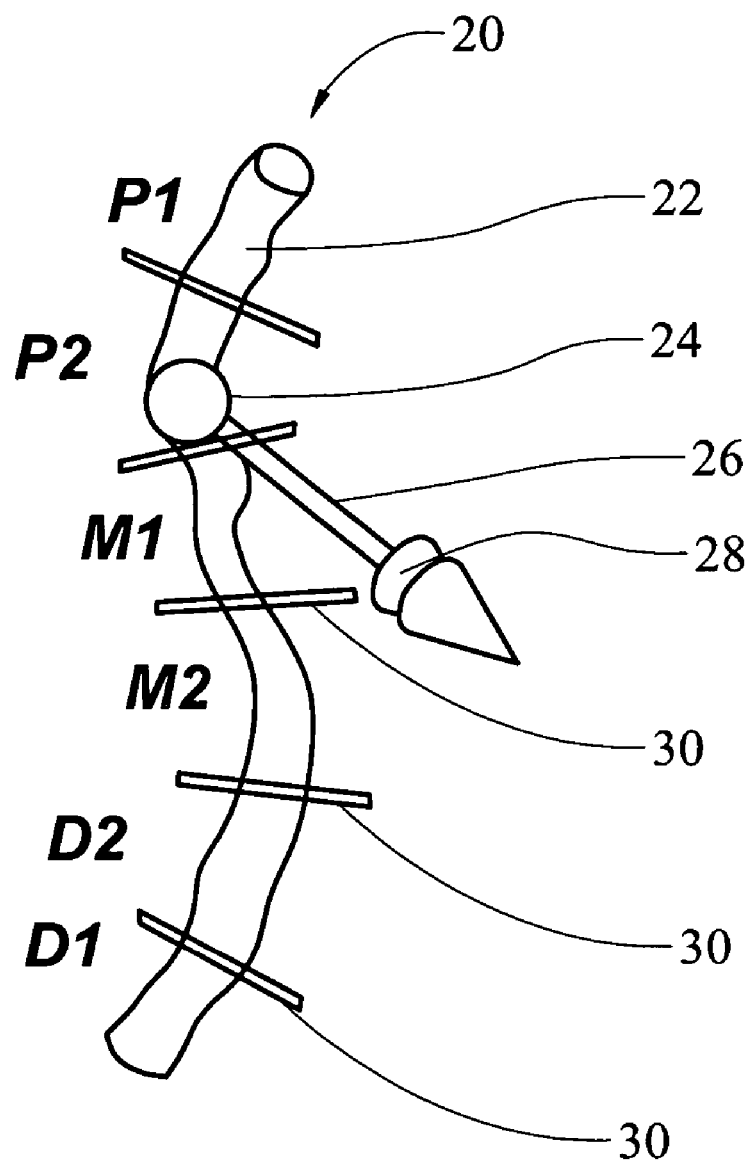
FIG. 3 is a view of the section of the exemplary body lumen after labeling the sections of the lumen or cavity.

As shown in FIG. 3 a medical device is being navigated through a body lumen such as a blood vessel. The blood vessel is divided into a plurality of named sections. The distal tip of the medical device is in section "P2" as indicated by the marker 24, and is heading toward section M1. The user attempting to navigate through the vessel can quickly and easily align the medical device with the particular section the device is being moved through vessel simply by calling out the displayed label for the appropriate section. For example, as the device is leaving section P2, the user might call out "P2" to align the device with the direction specified for section P2. Alternatively (depending upon how the associated direction for a section is selected), the user might call out "M1" to align the device with the direction specified with section M1. The user can then advance the device in the selected alignment.

Although the system might accept other commands from the user, knowing that the device is located in section P2 the system would not accept commands identifying sections other than P1, P2, and M1, because the user would not specify a section that was not the same as or adjacent to the section were the device is presently located. Alternatively, or in addition, the system could include a validation procedure such that after the user orally identifies a section, e.g. "M1" the label on the display 20 is highlighted (for example by color change) so that the user can confirm or reject the selection, such as by saying "ACCEPT" or "REJECT" or other appropriate command.

The direction associated with each section can be determined in a number of ways. The direction may be average or weighted average direction of the centerline. The direction may alternatively be the direction at one of the two ends of the segment (and which end may vary depending on whether the device is being advanced or retracted). The direction may also be the direction of the midpoint of the centerline. A direction on the centerline is convenient, because it is usually known from the reconstruction of the imaging data. Of course the method of determining the direction associated with each segment does not have to be the same for each segment, and this direction can be determined with different methods depending, for example of the curvature or rate of change of curvature of the lumen or the direction of travel, or other factors. In some cases imaging data may be spotty, and the direction associated with a particular segment may be based upon the adjacent segments. For example, it could be based on the directions associated with the adjacent segments, or the endpoints of the adjacent segments.

What is claimed:

1. A method of controlling a remote navigation system that remotely orients the distal end of the medical device in order to navigate a medical device through a body lumen or catheter, the method comprising:

introducing a medical device within a body lumen;

displaying on a display device an image of a body lumen or cavity divided into a plurality of segments in which the centerline direction of each segment does not vary by more than a predetermined angular amount;

displaying on the display device a label for at least one of the segments;

receiving oral commands using a system adapted to receive and process oral commands, and recognizing an oral identification of a particular segment label that is being displayed on the display device as an identified segment; and transforming the identified segment by causing the remote navigation system to orient the distal end of the medical device that is within the body lumen in a predetermined direction corresponding to the identified segment associated with the recognized segment label.

2. The method according to claim 1 further comprising superimposing an indicator of the current position of the medical device on the display device displaying the image of the body lumen or cavity.

3. The method according to claim 2 further comprising displaying on the display device an image of the portion of the body lumen through which the distal end of the medical device is being navigated, and indicating on the display device the present position of the distal end of the medical device by highlighting a ring on the surface of the displayed image of the body lumen in the plane perpendicular to the centerline of the lumen at the current position of the distal end of the catheter.

4. The method according to claim 1 wherein labels for a plurality of segments are displayed on the display device.

5. The method according to claim 1 wherein the predetermined direction associated with each segment is the average direction of the centerline of the segment.

6. The method according to claim 1 wherein the predetermined direction associated with each segment is the direction at the midpoint of centerline of the segment.

7. The method according to claim 1 wherein the predetermined direction associated with each segment is the direction at an end point of centerline of the segment.

8. The method according to claim 1 wherein the segments are automatically defined based upon a predetermined variance of centerline direction.

9. The method according to claim 1 wherein the segments are defined by the user.

10. The method according to claim 1 wherein the labels are automatically generated.

11. The method according to claim 1 wherein the labels are created by the user.

12. The method according to claim 1 wherein the image of the body lumen or cavity being displayed on the display device is generated from three-dimensional imaging data.

13. The method according to claim 1 wherein the image of the body lumen or cavity being displayed on the display device is generated from two two-dimensional images.

14. A method of controlling a remote navigation system that remotely orients the distal end of the medical device in order to navigate a medical device through a body lumen or catheter, the method comprising:

introducing a medical device within a body lumen;

processing imaging data of a body lumen or cavity to divide the lumen into a plurality of segments in which the centerline direction of each segment does not vary by more than a predetermined angular amount;

displaying on a display device an image of a body lumen or cavity divided into a plurality of segments in which the centerline direction of each segment does not vary by more than the predetermined angular amount;

displaying a label for a plurality of the segments;

receiving oral commands using a system adapted to receive and process oral commands, and recognizing in the oral commands an oral identification of a particular segment label that is being displayed on the display device as an identified segment; and transforming the identified segment by causing the remote navigation system to orient the distal end of the medical device that is within the body lumen in a predetermined direction corresponding to the identified segment associated with the recognized segment label.

15. The method according to claim 14 further comprising superimposing an indicator of the current position of the medical device on the display device displaying the image of the body lumen or cavity.

16. The method according to claim 15 further comprising displaying on the display device an image of the portion of the body lumen through which the distal end of the medical device is being navigated, and indicating on the display device the present position of the distal end of the medical device by highlighting a ring on the surface of the displayed image of the body lumen in the plane perpendicular to the centerline of the lumen at the current position of the distal end of the catheter.

17. The method according to claim 14 wherein labels for a plurality of segments are displayed on the display device.

18. The method according to claim 14 wherein the predetermined direction associated with each segment is the average direction of the centerline of the segment.

19. The method according to claim 14 wherein the predetermined direction associated with each segment is the direction at the midpoint of centerline of the segment.

20. The method according to claim 14 wherein the predetermined direction associated with each segment is the direction at an end point of centerline of the segment.

21. The method according to claim 14 wherein the segments are automatically defined based upon a predetermined variance of centerline direction.

22. The method according to claim 14 wherein the segments are defined by the user.

23. The method according to claim 14 wherein the labels are automatically generated.

24. The method according to claim 14 wherein the labels are created by the user.

25. The method according to claim 14 wherein the direction associated with at least one section is based at least in part upon the adjacent sections.

26. A method of controlling a remote navigation system that remotely orients the distal end of the medical device in order to navigate a medical device through a body lumen or catheter, the method comprising:

introducing a medical device within a body lumen;

processing image data of a body lumen to divide the body lumen into a plurality of segments in which the centerline direction of each segment does not vary by more than a predetermined angular amount;

displaying on a display device an image of a body lumen or cavity divided into a plurality of segments in which the centerline direction of each segment does not vary by more than the predetermined angular amount;

displaying a label for a plurality of the segments;

giving oral commands including the label associated with a segment of the body lumen or catheter to an interface system capable of recognizing the label;

receiving the oral commands using a system adapted to receive and process oral commands, and recognizing in the oral commands a particular segment label that is being displayed on the display device as an identified segment; and transforming the identified segment by operating the remote navigation system to orient the distal end of the medical device that is within the body lumen in a predetermined direction corresponding to the identified segment associated with the recognized segment label.

27. The method of claim 26, further comprising the steps of advancing the medical device under the control of the user, determining the position of a medical device in the body lumen; and automatically orienting the distal end of the medical device in the direction of the centerline of a particular identified segment of the lumen based on a voice command from the user.

* * * * *